United States Patent [19]
Armitage et al.

[11] Patent Number: 6,146,861
[45] Date of Patent: Nov. 14, 2000

[54] PROCESSES FOR THE PRODUCTION OF AMIDASE

[75] Inventors: Yvonne Christine Armitage; Jonathan Hughes, both of Huddersfield, United Kingdom

[73] Assignee: Ciba Specialty Chemicals Water Treatment Limited, West Yorkshire, United Kingdom

[21] Appl. No.: 09/011,025
[22] PCT Filed: Aug. 9, 1996
[86] PCT No.: PCT/GB96/01951
§ 371 Date: Jul. 24, 1998
§ 102(e) Date: Jul. 24, 1998
[87] PCT Pub. No.: WO97/06248
PCT Pub. Date: Feb. 20, 1997

[30] Foreign Application Priority Data

Aug. 9, 1995 [GB] United Kingdom .................. 9516346
Mar. 22, 1996 [GB] United Kingdom .................. 9606047

[51] Int. Cl.$^7$ .............................. C12P 13/00; C12P 7/62; C12N 9/78
[52] U.S. Cl. ................... 435/128; 435/71.1; 435/134; 435/135; 435/136; 435/146; 435/227; 435/252.1
[58] Field of Search ...................... 435/71.1, 227, 435/252.1, 128, 135, 134, 136, 146

[56] References Cited

FOREIGN PATENT DOCUMENTS

| | | |
|---|---|---|
| 0 255 390 A3 | 2/1988 | European Pat. Off. . |
| 0 329 324 A2 | 8/1989 | European Pat. Off. . |
| 0 329 325 A2 | 8/1989 | European Pat. Off. . |
| 0 362 829 A3 | 4/1990 | European Pat. Off. . |
| 0 393 916 A1 | 10/1990 | European Pat. Off. . |
| 0 444 640 A2 | 9/1991 | European Pat. Off. . |
| 0 502 476 A3 | 9/1992 | European Pat. Off. . |
| 63-2596 | 1/1988 | Japan . |
| 92/05205 | 4/1992 | WIPO . |

OTHER PUBLICATIONS

Bioscience, Biotechnology, and Biochemistry, vol. 57, No. 11, Nov. 1993, pp. 1949–1950, M. Kobayashi et al: "Occurrence of Amidases in the Industrial Microbe *Rhodococcus rhodochrous* J1".

Applied and Environmental Microbiology, Sep. 1994, pp. 3343–3348, M. Nawaz et al: "Purification and Characterization of an Amidase from an Acrylamide–Degrading Rhodococcus sp.".

Journal of Bacteriology, Sep. 1990, pp. 4807–4815, M. Kobayashi et al: "Purification and Characterization of a Novel Nitrilase of *Rhodococcus rhodochrous* K22 That acts on aliphatic Nitriles".

Biotechnology and Applied Biochemistry 11, 581–601 (1989), A. Goldlust et al: "Induction, Purification, and Characterization of the Nitrilase of *Fusarium oxysporum* f. sp. melonis".

Biotechnology and Applied Biochemistry 15, 283–302 (1992), D. Stevenson et al: "Mechanistic and Structural Studies on Rhodococcus ATCC 39484 Nitrilase".

Applied Microbiology Biotechnology (1990) vol. 34, pp. 322–324, T. Nagasawa et al: "Production of acrylic acid and methacrylic acid using *Rhodococcus rhodochrous* J1 nitrilase".

Primary Examiner—Herbert J. Lilling
Attorney, Agent, or Firm—David R. Crichton

[57] ABSTRACT

An amidase or nitrilase is made by continuous culture under carbon limitation using a carbon source which includes, respectively, either (a) an amide or amide precursor or (b) a nitrile or nitrile precursor. Novel enzymes have particular stability. A novel microorganism is *Rhodococcus rhodochrous* NCIMB 40756 and is capable of producing a particularly stable amidase. The novel amidase, and the amidase made by the defined process, are effective for converting (meth)acrylamide to ammonium (meth)acrylate, for instance in or after the polymerisation of the acrylamide.

9 Claims, No Drawings

PROCESSES FOR THE PRODUCTION OF AMIDASE

This invention relates to the production of enzymes by fermentation processes and the use of the enzymes as catalysts. It also relates to novel microorganisms particularly suitable for the production of certain improved enzymes.

It is known to convert amide molecules to their corresponding acid or acid salt. This is desired in particular in the case of acrylamide.

Conversion of (meth) acrylamide to its acid or salt is required on an industrial scale for production of (meth) acrylic acid monomer or a salt thereof.

Conversion of (meth) acrylamide to (meth) acrylic acid monomer is also desired for the purification of (meth) acrylamide homopolymer or copolymer of (meth) acrylamide with other monomers. Hydrolysis of residual (meth) acrylamide monomer is desirable as a way of meeting environmental concerns about the monomer.

It is known to use enzyme catalysts to hydrolyse residual monomeric (meth) acrylamide for the purification of (meth) acrylamide-containing polymers. Processes of this type are described in EP-A-0329324, EP-A-0329325 and WO92/05205.

It has also been suggested by Hawaz et al, in Applied and Environmental Microbiology, September 1994, p.3343–3348, that it would be desirable to use enzyme catalysts for the large scale production of acrylic acid if appropriate enzymes were available. In this paper Nawaz et al describe a Rhodococcus species which can use acrylamide as a growth substrate and produce an amidase enzyme. The bacterial cells were grown in batch culture.

It is generally found that when enzyme catalysts are used in the hydrolysis of monomeric (meth) acrylamide that the presence of the (meth) acrylamide monomer has a detrimental effect on the long term stability of the enzyme. There is a tendency for the enzyme catalyst to lose activity over time. This necessitates addition of further enzyme catalyst to return the catalytic activity to its original level. The lower the stability of the enzyme catalyst the less economical the process.

It is also known to convert nitrile molecules to their corresponding acid or acid salt. This can be carried out by the direct conversion of nitrile to acid using a nitrilase enzyme as catalyst. As used herein, a "nitrilase" is an enzyme which carries out the direct conversion of a nitrile to its corresponding acid without release of an amide intermediate. Nitrilases have been described in, inter alia, EP-A-444,640, JP-B-632596, Biotechnol. Appl. Biochem. 15, 283–302 (1992), Appl. Microbiol. Biotechnol. (1990) 34:322–324, Biotechnol. Appl. Biochem. 11, 581–601 (1989) and J. Bacteriol., September 1990, pages 4807 to 4815.

As with amidases, these enzymes often show a tendency to destabilise in the presence of large amounts of substrate (nitrile). As with amidases, instability results in a less economic process.

The normal way of cultivating microorganisms which produce an amidase or nitrilase is batch culturing. In this method an initial amount of the microorganism is placed in a growth medium containing a large excess of all nutrients necessary for growth of the microorganism. Growth proceeds either until it is terminated by harvesting the batch of cultured microorganism or until termination of growth due to exhaustion of nutrients or toxification of the growth medium due to build-up of by-products from the microorganism.

An alternative culture method is known as continuous culture. Continuous culture methods are generally known. In the most commonly used methods the culture, containing microorganism and growth medium and usually in liquid form, is continuously removed from the culture vessel and is replaced at the same rate with fresh growth medium so that the volume of liquid culture remains constant. Under steady state conditions the replication rate of the microorganism is governed by addition of new growth medium such that the biomass concentration of the culture is constant.

In continuous culture methods it is usual to provide one element which is metabolised to depletion in the culture medium and governs the steady state biomass concentration. This is known as the growth limiting element. All other elements are generally in excess.

EP-A-393916 describes a method of culturing a microorganism continuously under nitrogen limitation, which results in the microorganisms produced containing elevated levels of an amidase enzyme.

In GB-A-1379728 continuous culture appears to be conducted under conditions of carbon limitation, the carbon source being material such as glycerol, lactate or other material which can lead to Kreb's cycle intermediates. Preferably only one such carbon source is present in the culture medium.

It would be desirable to be able to produce an amidase or nitrilase enzyme improved in stability over the generally used enzymes. It would also be desirable to be able to produce an amidase or nitrilase enzyme having greater catalytic activity. In particular, it would be desirable to provide an enzyme which is particularly suitable for use as the enzyme in processes such as those described in WO92/05205 and EP-A-0329324 and EP-A-0329325.

According to a first aspect of the invention there is provided a process of producing an amidase or nitrilase enzyme comprising
   cultivating in continuous culture a microorganism capable of producing the enzyme in a growth medium comprising a carbon source
   wherein the culture is conducted under carbon limitation and wherein if an amidase enzyme is being produced the carbon source includes an amide or amide precursor and if a nitrilase enzyme is being produced the carbon source includes a nitrile or nitrile precursor.

It will be appreciated that in this process the microorganism is preferably an inducible microorganism, in contrast to the constitutive microorganism used in GB-A-1379728.

The invention reduces catabolite repression by limiting the amount of metabolite available (as a result of the carbon limitation). Catabolite repression has previously been proposed in some processes to increase yield but we surprisingly find that the process of the invention has a number of other advantages. The microorganisms produced by this process exhibit an enzyme activity per gram cell weight which is much improved over activity obtained in equivalent microorganisms produced by batch culturing methods.

A particularly unexpected advantage is the improvement in stability of the enzyme produced by the microorganisms cultivated according to the process of the invention, in comparison with enzyme produced by equivalent microorganisms obtained by batch culturing methods. In an acrylamide or acrylonitrile reactor the enzyme can show a decrease in activity over time which is greatly reduced in comparison with batch cultured enzymes of the same type.

The process can surprisingly yield enzyme of particular value for use in processes such as those described in EP-A-0329324 and 0329325 and, especially, WO92/05205.

In this invention when we say "continuous culture" we include the truly continuous processes commonly used. We also include any process of cultivating microorganisms which is not a true batch process. Thus we include semi-continuous processes. In a true batch process excess of all nutrients is present initially and growth is allowed to continue until it becomes self-limiting. In the invention the nutrient or nutrients which provide the growth-limiting element must be added continuously or semi-continuously to the culture vessel throughout growth, so that the growth-limiting element is never present in excess. A continuous process of the invention often involves continuous removal of microorganism as it grows. However, this is not essential. The process may be carried out for instance with excess of all elements except carbon being present initially and carbon being introduced gradually in order to limit rate of growth, which continues until the other nutrients are exhausted. Such processes are sometimes referred to as "fed batch" processes. In the invention truly continuous processes are preferred.

The process of the invention may be used to produce an amidase or nitrilase enzyme. Generally only one of these enzymes is produced in a single process, although it is possible to produce mixtures of enzyme. This can be done for instance by culturing a mixture of compatible microorganisms. Preferably the process of the invention is used to produce an amidase enzyme.

In the invention it is essential, where an amidase is produced, that the culture is conducted under carbon limitation. Other elements, for instance nitrogen, oxygen and phosphorus, are in excess. The exact proportions of these elements which are used in the growth medium will be determined by the composition of the particular microorganism being cultured and can be planned by establishing the relative amounts of these and other elements in the microorganism.

In the invention it is also essential, where an amidase is produced, that the source of carbon includes an amide or amide precursor. An amide precursor is a compound which can be metabolised to an amide by the microorganism being cultured or is otherwise converted to an amide in the growth medium.

Suitable amides include acrylamide, methacrylamide, acetamide and propionamide and N-substituted derivatives of these. Mixtures may be used. Acetamide is preferred.

Suitable amide precursors include nitriles such as acrylonitrile, methacrylonitrile and acetonitrile and mixtures thereof. Mixtures of amides and amide precursors may be used.

For production of amidase, the amide or amide precursor generally forms at least 20 mol %, preferably at least 30 mol % and more preferably at least 50 mol % of the total carbon source. Often the amide or amide precursor forms at least 80 mol % of the carbon source. Preferably the carbon source consists substantially only of amide and/or amide precursor.

It is particularly preferred, for production of amidase, for the carbon source to consist substantially only of acetamide or a precursor thereof.

In the invention it is essential, where a nitrilase is produced, that the source of carbon includes a nitrile or nitrile precursor. A nitrile precursor is a compound which can be metabolised to a nitrile by the microorganism being cultured or is otherwise converted to a nitrile in the growth medium.

Suitable nitriles include acrylonitrile, methacrylonitrile, acetonitrile and propionitrile. Mixtures may be used.

For production of nitrilase, the nitrile or nitrile precursor generally forms at least 20 mol %, preferably at least 30 mol % and more preferably at least 50 mole % of the total carbon source. Often the nitrile or nitrile precursor forms at least 80 mole % of the carbon source. Preferably the carbon source consists substantially only of nitrile and/or nitrile precursor.

Where the carbon source comprises an amide or mixture of amides this will generally contribute towards the nitrogen and oxygen components of the growth medium. Generally it will form only part of the oxygen source. The amide may form only part of the nitrogen component or it may provide the whole of the nitrogen component of the growth medium. Whether this is possible will depend on the composition of the microorganism being cultured. For instance, if the amide has a nitrogen:carbon ratio greater than that of the microorganism, it may be possible to provide the amide in amounts which result in a growth medium which is carbon-limited but contains excess nitrogen, both elements being provided solely by the amide. If the nitrogen:carbon ratio in the amide is lower than that of the microorganism being cultured it will generally be necessary to provide a further source of nitrogen in addition to the amide in order for nitrogen to be present in excess.

Similar considerations apply to nitriles as components of the carbon source. These can also contribute towards the nitrogen component of the growth medium.

The carbon source may also include other carbon-containing compounds in addition to the amide, amide precursor, nitrile or nitrile precursor. Suitable compounds are compatible with and capable of being metabolised by the microorganism and compatible with other components of the growth medium. Suitable compounds include carboxylic acids and derivatives thereof, alcohols, sugars, starches and other carbohydrates.

The growth medium should contain sources of all other necessary elements. These may include nitrogen, oxygen, phosphorus, sulphur, hydrogen, potassium, sodium, calcium, magnesium, copper, zinc, manganese, iron and other metals, chlorine and vitamins.

These materials may be provided in the form of any compound which can be metabolised by the microorganism. Suitable components of the growth medium include organic acids, for instance carboxylic acids and their alkali metal or ammonium salts; chlorides, sulphates and other salts of sodium, and the other metals listed above; acids of phosphorus and their salts; vitamins; salts of trace metals; amino acids.

The culture is conducted under conditions of pH and temperature suitable for the microorganism being cultured. The pH of the growth medium is generally between 6 and 8, preferably above 6.5. The pH may be below 7.5, and is often substantially neutral. The temperature which is most suitable for the culturing process will depend on the microorganism selected. Generally temperature is from 20 to 42° C., often 25 to 37° C.

If the microorganism chosen produces the required enzyme or enzymes constitutively then no special conditions are required to ensure the enzyme is produced. Certain microorganisms produce enzymes inducibly and therefore require special conditions, for instance particular constituents of the growth medium, in order to induce them to produce the required enzyme. Induction of enzyme production can be carried out in any known manner. For instance, nitrilase may be induced as described in Biotechnol. Appl. Biochem. 15, 283–302 (1992), then Biotechnol. Biochem. 11, 581–601 (1989) or Appl. Microbiol. Biotechnol. (1990) 34:322–324 and EP-A-444,640.

The method of the invention may be used to produce any amidase or nitrilase enzyme. Known microorganisms which are suitable for producing an amidase enzyme include bacterial sources, for instance strains of the genera Brevibacterium, Pseudomonas, Alcaligenes, Arthrobacter, Corynebacterium, Mycobacterium, Lactobacillus, Micrococcus, Nocardia, Strentomyces, Rhodococcus, Microbacterium, Bacteridium and mixed cultures of Brevibacterium and Bacillus. Suitable yeast and fungi include strains of Fusarium and Aspergillus. Suitable bacterial sources for nitrilase include strains of the genera Corynebacterium, Nocardia, Bacillus, Bacteridium, Micrococcus and Brevibacterium, for instance *Rhodococcus rhodochrous* J1, Rhodococcus ATCC 39484, *Rhodococcus rhodochrous* K22, *Fusarium oxysporum* and *Pseudomonas chloraraphis*.

A particularly preferred microorganism is the novel microorganism also provided by the invention. This is a microorganism which is *Rhodococcus rhodochrous* strain NCIMB 40756 or mutant thereof having the ability to produce an amidase. A sample of this strain was deposited at the National Collections of Industrial and Marine Bacteria Limited (NCIMB), 23 St. Machar Drive, Aberdeen AB2 1RY, Scotland, UK on Jul. 14, 1995 under the Budapest Treaty and has the accession number NCIMB 40756. All restrictions imposed by the depositor on the availability to the public of the deposited biological material will be irrevocably removed upon the granting of the patent.

The above strain showed the following results on analysis:

The cell wall diamino acid is meso DAP. Mycolic acids are present. The fatty acid profile shows the following acids in the indicated percentages:

| | |
|---|---|
| tetradecanoic | 14.6% |
| hexadecenoic | 19.0% |
| hexadecanoic | 19.4% |
| octadecenoic | 23.5% |
| tuberculostearic (10-methyloctadecanoic) | 25.2%. |

Biochemical testing gave the following results:

| | 10 days, 30° C. |
|---|---|
| Decomposition of: | |
| Adenine | + |
| Tryrosine | + |
| Urea | − |
| Decomposition of: | |
| Inositol[1] | − |
| Maltose[1] | + |
| Mannitol[1] | + |
| Rhamnose[1] | − |
| Sorbitol[1] | + |
| m-hydroxybenzoic acid[2] | (+) |
| Sodium adipate[2] | − |
| Sodium benzoate[2] | + |
| Sodium citrate[2] | + |
| Sodium lactate[2] | + |
| Sodium glutamate[2] | − |
| L-tyrosine[2] | + |
| Glycerol[1] | + |
| Trehalose[1] | − |
| p-hydroxybenzoic acid[2] | + |
| D-mannose[1] | (+) |
| Acetamide[2] | + |
| D-galactose[1] | − |
| Enzymatic tests: | |
| α-glucosidase | + |
| Cysteine arylamidase | − |
| Valine arylamidase | − |
| Growth in the presence of: | |
| 5% NaCl | + |
| Sodium azide[3] | − |

[1] 1% w/v
[2] 0.1% w/v
[3] 0.02% w/v
(+) weak positive

This strain is capable of producing amidase enzyme.

A further preferred microorganism is *Rhodococcus rhodochrous* strain NCIMB 40757 or a mutant thereof having the ability to produce a nitrilase. A sample of this strain was deposited at the National Collections of Industrial and Marine Bacterial Limited (NCIMB), 23 St. Machar Drive, Aberdeen AB2 1RY, Scotland, UK on Aug. 8, 1995 in accordance with the provisions of the Budapest Treaty and has the accession number NCIMB 40757.

The strain deposited under NCIMB 40757 showed the following results on analysis:

The cell wall diamino acid is meso DAP. The fatty acid profile shows the following acids in the indicated percentages:

| | |
|---|---|
| tetradecanoic | 2.1% |
| pentadecanoic | 2.8% |
| hexadecenoic | 24.7% |
| hexadecanoic | 25.9% |
| heptadecenoic | 6.2% |
| heptadecanoic | 3.1% |
| octadecenoic | 25.0% |
| octadecanoic | 1.9% |
| tuberculostearic | 7.0%. |

Biochemical testing gave the following results:

| | |
|---|---|
| Decomposition of: | |
| Adenine | − |
| Tyrosine | + |
| Urea | − |
| Growth in Presence of: | |
| 5% NaCl | + |
| Dextrose azide | (+) |
| Growth on sole carbon sources: | |
| Inositol | (+) |
| Maltose | + |
| Mannitol | + |
| Rhamnose | − |
| Sorbitol | + |
| m-hydroxybenzoic acid | + |
| Sodium adipate | + |
| Sodium benzoate | + |
| Sodium citrate | + |
| Sodium lactate | + |
| Sodium glutamate | − |

| | |
|---|---|
| -continued | |
| L-tyrosine | + |
| Glycerol | + |
| Trehalose | + |
| p-hydroxybenzoic acid | + |
| D-mannose | + |
| Acetamide | + |
| D-galactose | (+) |
| Enzyme Tests: | |
| Rosco discs. 4 hours. 37° C. | |
| α-glucosidase | − |
| Cysteine arylamidase | − |
| Valine arylamidase | − |

(+) weak positive

This strain is capable of producing nitrilase enzyme and is described in further detail in our copending Application No. 9525372.0.

Yields and specific activities, and also other characteristics of the microorganism cultivated in the method of the invention, may be improved by selection procedures, eg after mutagenesis.

Amidase enzymes produced by the process of the invention may be used for the conversion of amides to their corresponding acids or salts, Thus a second aspect of the invention also comprises a method of converting an amide to the corresponding acid or acid salt comprising producing an amidase enzyme by cultivating in continuous culture a microorganism capable of producing an amidase enzyme in a growth medium comprising a carbon source which includes an amide or amide precursor wherein the culture is conducted under carbon limitation and introducing the enzyme into an environment containing the amide.

This method is particularly useful for the conversion of unsaturated amides to their corresponding unsaturated acids or acid salts. Suitable amides include acrylamide and methacrylamide, which are converted into ammonium (meth) acrylate, which can then be further reacted to form (meth) acrylic acid or other salts if desired.

The method of the second aspect of the invention may be used for the purification of polymers which have been formed from acrylamide monomer, with or without comonomer (polyacrylamides). This purification may be carried out in any conventional manner, for instance as described in U.S. Pat. No. 4,687,807 or in EP-A-0329,324 and EP-A-0329,325. Thus the enzyme may be maintained in contact with the polymer in particulate form in a reverse phase emulsion (which may be dehydrated) or it may be contacted with polymer gel which may then be dried. The enzyme has good activity when the emulsion or gel is maintained in contact with the enzyme at elevated temperatures, e.g. 40 to 95° C., especially 50 to 80° C.

The concentration of acrylamide monomer in a polyacrylamide environment may be as high as 2,000 ppm and is generally from 100 to 1,000 ppm, often 200 to 1,000 ppm. The enzyme may be used to effect a reduction in the acrylamide monomer content of the polyacrylamide. Where the original acrylamide monomer content is relatively high, for instance around 2,000 ppm, the method of the invention can effect a reduction to 500 ppm or below. Where the concentration of acrylamide monomer is lower, for instance up to 1,000 ppm, monomer levels can be reduced to below 200 ppm or even as low as 50 ppm or 10 ppm or less.

In a preferred process of the invention, we make a polymer of (meth) acrylamide by a process which comprises providing an aqueous polymerisable mixture containing (meth) acrylamide in a reaction vessel, exothermically polymerising the polymerisable mixture and recovering the resultant polymer from the reaction vessel, and in this process the residual (meth) acrylamide content of the polymer is reduced by incorporating in the polymerisable mixture the amidase made by the process of the invention.

The method of the second aspect of the invention may also be used for industrial scale production of ammonium acrylate by hydrolysis of acrylamide. The ammonium acrylate may be converted to a different salt or to the acid form or may be used directly as a monomer in polymerisation processes.

The acrylamide conversion method of the invention can be a continuous process. In such a process the concentration of ammonium acrylate in the reactor and thus in the reactor output is preferably from 5 to 25%, more preferably not more than 20%, most preferably 10 to 15%. High concentration acrylamide (for instance a 300 to 400 g/l solution) is fed into the reactor to maintain a concentration of acrylamide of for instance 3 to 45 g/l, often 20 to 30 g/l.

Preferably however the acrylamide conversion method of the invention is a fed batch process. In such a process high concentration acrylamide (for instance a 300 to 400 g/l solution) is fed into a reactor containing the amidase enzyme and the concentration of ammonium acrylate is allowed to rise to a specified value, for instance 5 to 25%, preferably at least 10%, often 15 to 20%, and the reaction is then stopped. During the reaction the acrylamide concentration is preferably maintained at from 3 to 45 g/l, preferably at least 15 g/l, generally around 27 to 30 g/l.

The amidase enzyme may be introduced into the reaction mixture (containing acrylamide monomer or impure polyacrylamide) in any suitable form. It may for instance be introduced in the pure form, having been extracted from the cultured microorganism before use as a catalyst. The extraction method used should ensure that the activity and stability of the enzyme are not lost.

It may also be introduced in a semi-pure form, for instance as liquid culture or a bacterial cell fraction such as intact cells or crushed cells. The amidase may be introduced as a crude, impure enzyme solution. It may be supported or immobilised on a carrier. Suitable carriers include cross-linked polymeric matrix, for instance cross-linked polyvinyl alcohol or cross-linked polyacrylamide. The enzyme may be incorporated into a carrier in any suitable form, for instance as pure, extracted enzyme or as intact bacterial cells. Preferably the amidase enzyme is introduced in the form of intact bacterial cells or supported in a cross-linked polymeric matrix.

The amide conversion reaction is generally carried out at a temperature of from 0 to 50° C., often 4 to 30° C.

We find that in this amidase conversion method the enzyme produced according to the process of the invention gives far greater stability than the batch-produced enzymes previously used. In particular the half-life (period taken for enzymic activity to drop to half its original level) of the amidase enzyme used in the method of the invention can be increased two-, four- and often tenfold in comparison with equivalent amidase enzymes produced using the same microorganisms by batch methods.

Nitrilase enzyme produced by the process of the invention may be used for the conversion of nitriles to their corresponding acid (or salt).

A third aspect of the invention comprises a method of converting a nitrile to its corresponding acid or acid salt comprising producing a nitrilase enzyme by cultivating in continuous culture a microorganism capable of producing a nitrilase enzyme in a growth medium comprising a carbon source which includes a nitrile or nitrile precursor wherein the culture is conducted under carbon limitation and introducing the enzyme into an environment containing the nitrile.

This method is particularly useful for conversion of unsaturated nitriles. Suitable nitriles include acrylonitrile and methacrylonitrile, which are converted into ammonium (meth) acrylate.

The method of the third aspect of the invention may be used for the purification of polymers which have been formed from (meth) acrylonitrile monomer, with or without comonomer. This purification may be carried out in any known manner.

The method of the third aspect of the invention may also be used for industrial scale production of ammonium acrylate. Conditions should be chosen to allow optimum activity of the enzyme and may be conventional.

Enzyme may be introduced into the reaction mixture in any of the forms described above for amidase. The nitrile conversions are generally carried out at temperatures of from 0 to 50° C., often 4 to 30° C.

Nitrile conversion processes in which the nitrilase can be used are described in our co-pending applications having numbers 9525372.0 and 9525374.6.

The nitrilase enzyme produced according to the process of the invention again has stability to the reaction mixture greater than batch-produced equivalent enzymes.

The enzyme product of the continuous culture process of the invention is a novel product in itself. Accordingly a fourth aspect of the invention also provides an amidase or nitrilase enzyme obtainable by a process comprising cultivating in continuous culture a microorganism capable of producing the enzyme in a growth medium comprising a carbon source wherein the culture is conducted under carbon limitation and wherein if an amidase enzyme is being produced the carbon source includes an amide or amide precursor and if a nitrilase enzyme is being produced the carbon source includes a nitrile or nitrile precursor.

The product is obtainable by any of the processes discussed above in conjunction with the process of the first aspect of the invention. Preferably the product is an amidase enzyme.

It is not clear as yet exactly why the enzyme product of the invention gives its improved results. It is possible that in microorganisms capable of producing more than one form of amidase or nitrilase enzyme the conditions of the continuous culturing process of the invention induce production of a more stable form in preference to a less stable form. This stability may be due to higher molecular weight or to a different amino acid sequence. It is also possible that the enzyme produced according to the invention has a quaternary structure different from equivalent batch-produced enzymes; for instance it may be in the form of an aggregate of two or more protein sub-units.

The product of the invention is preferably an amidase and obtainable by a process as described above in which the source of carbon is substantially only acetamide and in which the microorganism is *Rhodococcus rhodochrous* strain NCIMB 40756 or a mutant thereof able to produce an amidase, or one whose yield and other characteristics have been improved by selection procedures, eg after mutagenesis.

The enzyme product of the invention may be prepared from microorganisms but it may also be prepared by cloning, using conventional techniques.

The preferred amidase product of the invention exhibits excellent stability in the presence of amides which it is required to hydrolyse. In particular, the invention provides an amidase enzyme which has a half-life t½ of 80 to 300 days, preferably 126 to 200 days, at 5° C. in an aqueous environment at pH 7 in a sequential fed batch process in which the acrylamide concentration is 27 g/l to 30 g/l and the ammonium acrylate concentration rises from 0 to 150 g/l in each batch. In this test, "days" are days of reaction and do not include dormant days between batches.

The invention also includes the use of the novel enzymes and/or microorganisms that will produce them for converting (meth) acrylamide to ammonium (meth) acrylate either in bulk or in a polymer of acrylamide, e.g. as described in EP-A-0329324 and EP-0A-0329325. In particular the invention includes making a polymer of (meth) acrylamide by a process which comprises providing an aqueous polymerisable mixture containing (meth) acrylamide in a reaction vessel, exothermically polymerising the polymerisable mixture and recovering the resultant polymer from the reaction vessel, and in this process the residual (meth) acrylamide content of the polymer is reduced by incorporating in the polymerisable mixture the novel enzyme and/or microorganism.

Generally the polymerisation proceeds exothermally to a temperature that in commercial practice is nearly always well above 50° C., typically above about 55 or 60° C. and often above about 70° C., e.g. up to 80 or 90° C. Generally the entire temperature rise is due to the exotherm and the process of the invention is preferably conducted on a polymerisable mixture that has a concentration such that there will be an exothermic rise of at least 20° C. and often at least 30° C. and frequently at least 40° C., e.g. to a temperature of 80 or even 90° C.

Thus in the invention the amidase is incorporated in the polymerisable mixture, generally before any polymerisation occurs, and so is exposed to the presence of a large amount of monomer and to the significant exotherm, and it would have been thought that these two conditions would have been undesirable. However we have surprisingly found that the enzyme of the invention is effective under these conditions.

The enzyme and/or microorganism may be used in the manner and in the processes described in EP-A-0329324, EP-A-0329325 and WO92/05205.

The entire disclosure of each of those published Applications of Allied Colloids Limited and David Farrar is hereby incorporated by reference.

The product of the invention may alternatively be a nitrilase. This enzyme is also highly stable in the presence of reaction mixture.

The invention will now be illustrated with reference to the following examples.

EXAMPLE 1

The original isolate *Rhodococcus rhodochrous* strain NCIMB 40756 grown in batch culture and containing amidase enzyme or in which amidase enzyme can be induced is transferred to continuous culture. The culture medium, which is shown in the table below, is designed to grow *Rhodococcus rhodochrous* strain NCIMB 40756 continuously under carbon limitation, where acetamide is the sole carbon and nitrogen source.

| Component | Amount present/liter |
|---|---|
| $K_2HPO_4$ | 7 g |
| $KH_2PO_4$ | 3 g |
| Acetamide | 1.1 g |
| NaCl | 0.1 g |
| $CaCl_2.6H_2O$ | 0.2 g |
| $MgSO_4.7H_2O$ | 0.5 g |
| Vitamins | 0.1 ml |
| Trace Metals | 1 ml |

Under steady-state culture at a dilution rate of 0.04 $h^{-1}$, (achieved during the period from 160 to 390 hours), elevated levels of specific amidase activity were observed, as shown in Table 1 below.

TABLE 1

| Culture time (hrs) | Specific Amidase Activity (U/mg) | Biomass (g/l) |
|---|---|---|
| 0 | not measured | 0.10 |
| 50 | not measured | 0.10 |
| 100 | 11 | 0.09 |
| 150 | 22 | 0.52 |
| 200 | 9 | 0.31 |
| 250 | 12 | 0.34 |
| 300 | 16 | 0.37 |
| 350 | 15 | 0.34 |
| 390 | 15 | 0.31 |

COMPARATIVE EXAMPLE 1

The original isolate *Rhodococcus rhodochrous* strain NCIMB 40756 grown in batch culture and containing amidase enzyme or in which amidase enzyme can be induced is transferred to batch culture. The initial composition of the batch culture medium is shown in the table below.

| Component | Amount Present/liter |
|---|---|
| $K_2HPO_4$ | 7 g |
| $KH_2PO_4$ | 3 g |
| Acetamide | 2 g |
| Sodium Acetate | 10 g |
| $CaCl_2.6H_2O$ | 0.1 g |
| $MgSO_4.7H_2O$ | 0.5 g |
| Vitamins | 0.1 ml |
| Trace Metals | 1 ml |

During batch culture comparatively low specific amidase activity was observed. Results are shown in Table 2 below.

TABLE 2

| Culture time (hrs) | Specific Amidase Activity (U/mg) | Biomass (g/l) |
|---|---|---|
| 0 | not measured | 0.10 |
| 2 | not measured | 0.10 |
| 4 | not measured | 0.15 |
| 6 | not measured | 0.20 |
| 7 | 2.6 | 0.25 |

TABLE 2-continued

| Culture time (hrs) | Specific Amidase Activity (U/mg) | Biomass (g/l) |
|---|---|---|
| 8 | 2.4 | 0.30 |
| 10 | 2.3 | 0.75 |
| 12 | 2.6 | 1.70 |

EXAMPLE 2

The cells of the *Rhodococcus rhodochrous* strain grown as described in Example 1 are immobilised in cross-linked polyacrylamide beads as follows:

a paste consisting of cells separated from the culture medium is suspended in chilled buffer and added to a mixture of monomer and cross-linker also in chilled buffer. The water-soluble component of a redox initiator system is added immediately afterwards. The cell/monomer/initiator mixture is then transferred to a stirred resin pot containing mineral oil and chilled surfactant and the second redox initiator component, soluble in both liquid phases, is added to initiate polymerisation. Upon polymerisation the cells are entrapped in the cross-linked polymer beads.

The amidase-active immobilised cells are transferred to a reactor and suspended in water at 5° C. and acrylamide added to give a concentration of 30 g/l. The amidase in the immobilised cells catalyses the hydrolysis of the acrylamide to produce ammonium acrylate. When the reactor acrylamide concentration is reduced to 27 g/l, sufficient acrylamide solution (at a concentration of 355 g/l), is automatically added to the reactor to raise the acrylamide concentration to 30 g/l. This automatic feeding procedure continues until the reactor ammonium acrylate concentration has risen to 150 g/l. Upon completion of a batch, which takes around 18 hrs, the immobilised *Rhodococcus rhodochrous* strain NCIMB 40756 cells are separated from the suspending monomer solution, resuspended in water and acrylamide added in a repetition of the procedure described above. The specific amidase activity is determined from the time taken for a known quantity of cells to complete a batch and the specific yield is determined from the amount of ammonium acrylate produced during a series of batches, as follows:

$$\text{Specific Yield } (g/g) = \frac{(\text{Mass of Ammonium Acrylate Produced})}{(\text{Mass of cells})}$$

$$\text{Specific Amidase Activity } (\mu moles/min/g) = \frac{(\text{Specific Yield})}{(\text{Times taken} \times 89)}$$

Results are shown in Table 3 below. The half life of the amidase was 126 days.

| Reactor Operation Time (days) | Specific Yield (g ammonium acrylate per g dry weight cells) | Specific Amidase Activity (μmoles/min/g dry weight cells) |
|---|---|---|
| 2 | 75 | 255 |
| 4 | 130 | 254 |
| 6 | 200 | 252 |
| 8 | 260 | 250 |
| 10 | 320 | 248 |
| 12 | 390 | 247 |
| 14 | 450 | 245 |
| 20 | 610 | 230 |
| 22 | 660 | 225 |

COMPARATIVE EXAMPLE 2

Cells of the *Rhodococcus rhodochrous* strain grown as described in Comparative Example 1 are immobilised in cross-linked polyacrylamide beads in the same way as described in Example 2. The amidase-active immobilised cells are transferred to a reactor and suspended in water at 5° C. and acrylamide added to give a concentration of 30 g/l. The remaining procedure is as described in Example 2. Results are shown in Table 4 below.

| Reactor Operation Time (days) | Specific Yield (g ammonium acrylate per g dry weight cells) | Specific Amidase Activity (μmoles/min/g dry weight cells) |
|---|---|---|
| 2 | 20 | 83 |
| 4 | 35 | 67 |
| 6 | 48 | 52 |
| 8 | 57 | 42 |
| 10 | 66 | 38 |
| 12 | 73 | 35 |

The results above show the improved stability and overall productivity of the amidase enzymes produced by the process according to the present invention. The activity of the amidase of the invention was consistently considerably greater than that of the amidase produced by batch culture. Furthermore, the amidase of the invention retained a far greater proportion of its activity over time. For instance the amidase of the invention underwent a drop of 8 U/g in activity in the period from 2 to 12 days, i.e. 3.1%. The amidase produced by the batch cultured microorganism underwent a drop of 48 U/g in the same period, that is 56.5%. The half-life of the enzyme was 8 days.

What is claimed is:

1. A process for producing amidase or nitrilase enzyme comprising
    a) cultivating a microorganism capable of producing the enzyme in continuous culture in a growth medium comprising a carbon source wherein the culture is conducted under carbon limitation and wherein when an amidase enzyme is being produced the carbon source includes an amide or amide precursor and when a nitrilase enzyme is being produced the carbon source includes a nitrile or nitrile precursor, wherein the microorganism is *Rhodococcus rhodochrous* strain NCIMB 40756 or a mutant thereof having the ability to produce an amidase; and
    b) recovering the resulting enzyme.

2. A process according to claim 1 in which the carbon source consists of one or more amides or nitrites.

3. A process according to claim 1 in which the enzyme is an amidase.

4. A process according to claim 3 in which an amidase is produced and the carbon source is substantially only acetamide.

5. A method of converting an amide to the corresponding acid or acid salt comprising
    a) introducing an amidase enzyme into an environment containing an amide wherein the amidase
        (1) has been produced by a process comprising cultivating a microorganism capable of producing the enzyme in continuous culture in a growth medium comprising a carbon source wherein the culture is conducted under carbon limitation and wherein the carbon source includes an amide or amide precursor or
        (2) is an amidase having a half-life t½ of 80 to 300 days in an aqueous environment at pH7 in a sequential fed batch process in which the acrylamide concentration is 27 g/l to 30 g/l and the ammonium acrylate concentration rises from 0 to 150 g/l in each batch or
        (3) is introduced by means of a microorganism which is *Rhodococcus rhodochrous* strain NCIMB 40756 and
    b) recovering the corresponding acid or acid salt of said amide.

6. A method according to claim 5 in which the amide is acrylamide and is converted to ammonium acrylate.

7. A method according to claim 5 in which the concentration of amide in the amide-containing environment is at least 15 g/l.

8. A method according to claim 5 in which the amide is residual acrylamide monomer contaminating a polyacrylamide or copolymer of acrylamide with other monomer or monomers and the amidase or microorganism is contacted with the polymer at a temperature of 40 to 95° C.

9. A method according to claim 5 comprising incorporating the enzyme or microorganism in an aqueous polymerisable mixture comprising (meth)acrylamide in a reaction vessel, exothermically polymerising the mixture and recovering the resultant polymer from the reaction vessel, whereby the inclusion of the enzyme or microorganism produces a resultant polymer that contains less (meth)acrylamide than a resultant polymer wherein no enzyme or microorganism has been included.

* * * * *